United States Patent [19]

Vartan

[11] Patent Number: 4,898,728

[45] Date of Patent: Feb. 6, 1990

[54] PROCESS FOR PRODUCTION OF COMPOSITION CONTAINING LECITHIN AND POLYVINYLPYRROLIDONE

[75] Inventor: Robert R. Vartan, Bristol, Tenn.

[73] Assignee: Beecham Group p.l.c., England

[21] Appl. No.: 178,487

[22] Filed: Apr. 7, 1988

[51] Int. Cl.$^4$ .................... A61K 31/79; A61K 31/74; A61K 31/43
[52] U.S. Cl. ........................................ 424/80; 424/78
[58] Field of Search .................................... 424/80, 78

[56] References Cited

U.S. PATENT DOCUMENTS 3,634,586 1/1972 Kaser ..................................... 424/80
4,316,886 2/1982 Taskis ..................................... 424/80

FOREIGN PATENT DOCUMENTS 1532993 11/1978 United Kingdom .................. 424/80

*Primary Examiner*—Joseph L. Schofer
*Assistant Examiner*—Carmen B. Pili-Curtis
*Attorney, Agent, or Firm*—Jacobs & Jacobs

[57] ABSTRACT

A process for the production of a sterile composition containing lecithin and polyvinyl pyrrolidone is disclosed in which the lecithin and polyvinyl pyrrolidone, optionally with one or more preservative powders are admixed in a solvent comprising about 75% to 90% methyl isobutyl ketone and about 10% to 25% isopropyl alcohol, and the solution passed through a millipore filter in order to render the ingredients sterile. The process is usefully employed in the production of injectable compositions of amoxycillin and ampicillin.

10 Claims, No Drawings

PROCESS FOR PRODUCTION OF COMPOSITION CONTAINING LECITHIN AND POLYVINYLPYRROLIDONE

The present invention relates to processes for the production of injectable compositions containing a β-lactam antibiotic such as amoxycillin trihydrate or ampicillin trihydrate.

An injectable composition of amoxycillin which provides unusually sustained effective levels of the antibiotic in the blood of humans and domestic animals after conventional administration has been disclosed and claimed in UK patent No. 1532993. The composition disclosed therein comprises an aqueous suspension of a powder comprising fine particles of amoxycillin trihydrate coated with a dispersing agent the ratio of amoxycillin trihydrate to dispersing agent being in the range 1000:1 to 20:1. A sterile composition in accordance with this patent containing amoxycillin trihydrate particles, a dispersing agent which is a mixture of lecithin and polyvinyl pyrrolidone, a preservative which is a mixture of methyl and propyl esters of p-hydroxy benzoic acid, a buffer such as sodium citrate and an ionic salt such as sodium chloride is commercially available from Beecham Group plc under the Trade Mark AMOXI-INJECT.

A number of processes are disclosed in the patent for effecting sterilisation of the compositions disclosed and claimed therein. One process comprises subjecting a non-sterile mix of all of the ingredients to ethylene oxide gas for 12 hours at appropriate temperature and pressure conditions followed by remilling under sterile conditions. An alternative process comprises sterilisation of the mixture by irradiation with an appropriate Megarad dose.

A more desirable process for commercial use involves the use of sterile amoxycillin trihydrate and sodium salts. The remaining ingredients must be completely dissolved and may then be rendered sterile by passage through a millipore filter and the sterile solution then aseptically combined with the sterile powders. Of the solvents known to dissolve all of these ingredients, only methylene dichloride is suitable on the grounds of cost and flammability. Thus chloroform, disclosed in U.K. patent No. 1532993 as a solvent for the ingredients is far too dangerous a chemical to be used freely in the factory. Unfortunately however use of methylene dichloride would be undesirable on environmental grounds.

The present invention is based on the discovery that solvents in which, individually, lecithin and polyvinyl pyrrolidone are insoluble can be admixed in a particular ratio to render these ingredients soluble.

According to the present invention there is provided an improved process for the production of a sterile composition containing lecithin and polyvinyl pyrrolidone, the improvement comprising admixing the lecithin and polyvinyl pyrrolidone optionally with one or more preservative powders, in a solvent comprising about 75% to 90% methyl isobutylketone and about 10% to 25% isopropyl alcohol, and passing the solution through a millipore filter in order to render the ingredients sterile.

Preferably the solvent contains essentially 80% to less than 90% methyl isobutyl ketone and more than 10% to 20% isopropyl alcohol. The most preferred solvent system comprises essentially 85% methyl isobutyl ketone (MIBK) and 15% isopropyl alcohol (IPA).

In use sufficient solvent must be used such that the solution formed is filterable through the millipore filter. It has been found that the vapour pressure of the solvent system used in the process of the invention is sufficiently high to facilitate efficient removal of solvent with gentle heat and vacuum. Moreover the use of the process of the invention totally overcomes the threat to the environment presented by use of large amounts of methylene chloride in a production facility.

A suitable millipore filter system for use in the process of the invention is a 5 μm polypropylene prefilter followed by a Nylon 66, 0.2 μm filter.

Normally Food Grade Lecithin powder is used in processes of the invention. Lecithin is known to be insoluble in solvents such as acetone, ethanol and methanol and is also insoluble in isopropyl alcohol. The polyvinyl pyrrolidone used must be of a parenteral grade such as Plasdone C-15 (Plasdone is a Trade Mark). Polyvinyl pyrrolidone may also be referred to by the generic name "Povidone USP". Povidone is insoluble in both acetone and methylisobutyl ketone.

Preferably preservative powders are also dissolved in the MIBK/IPA solvent system in processes of the invention. A preferred preservative is an ester of p-hydroxybenzoic acid, and in particular a mixture of methyl p-hydroxybnnzoate and propyl p-hydroxybenzoate. A commercial source of these preservative powders are known as methylparaben NF and propylparaben NF respectively.

The improved process of the present invention may be used in the production of sterile compositions containing amoxycillin, such as for example the composition marketed under the Trade Mark AMOXI-INJECT. The process may also be used in the production of sterile compositions containing ampicillin trihydrate coated with lecithin/polyvinyl pyrrolidone. The process may also be used in the production of mixtures of antibiotics in which a lecithin/polyvinyl pyrrolidone combination is used as a granulating and/or coating agent. Such compositions comprise a combination of amoxycillin trihydrate with ampicillin trihydrate, or either of the two in combination with one or more of the following antibiotics: sodium ampicillin, methicillin, cloxacillin, flucloxacillin or naphthacilline in the form of a sparingly soluble salt or coated with a suspending agent. The ratio of a second antibiotic to amoxycillin trihydrate is normally in the range from 5:1 to 1:5; for example 1:1.

The compositions produced by processes of the present invention may also contain conventional pharmaceutically acceptable additives used in the preparation of injectable compositions; such conventional additives include buffers and salts required to render the final injectable suspension of suitable tonicity. These additives are preferably used in a sterile form and are added to the sterile drug by direct blending.

Normally the buffers which may be used will be chosen so that the pH of the injectable suspension will enhance the stability of the suspension, for example the pH of the suspension will normally be from 5 to 8.5 and more usually 5.5 to 6.5. Suitable buffers for this purpose include sodium salts of organic acids, for example trisodium citrate, sodium acetate and the like or physiochemically similar salts such as the sodium salts of phosphoric acid, for example, di-sodium phosphate. Frequently the compositions produced will contain from 2-6% of such salts based on the total weight of the composition.

If the compositions produced by the process of the invention are to be made up into the injectable suspension by the addition of normal saline or the like then it is not usual to include additional ionic salts in the powder. However, if the compositions of the invention are to be made up by the addition of sterile water, then it is advantageous to include at least one ionic salt and this will usually be a sodium salt of a strong acid. It has been found that sodium chloride is particularly useful for this purpose. Normally the compositions will include up to 2% of sodium chloride expressed relative to the weight of amoxycillin trihydrate present and preferably 0.5-1% of sodium chloride.

Compositions produced by processes of the invention are normally presented in unit or multi dose form in vials or ampoules. When intended for human use these will normally contain, for example, between 100 and 1200 mg of amoxycillin trihydrate, and for large animal therapy between 1.5 g and 25 g, for example around 3 g. A suitable dose rate for animal therapy is about 3 to 20 mg/kg of amoxycillin trihydrate (measured as amoxycillin). In use the sterile contents of the vial or ampoule are mixed with an aqueous vehicle to form a suspension having good stability. This suspension is normally parenterally administered intra muscularly or sub-cutaneously. However intravenous and intraperitoneal administration may also be used. The prolonged blood levels given by such compositions in cattle, sheep, pigs, horses, goats, dogs and cats and the like enable very good blood levels to be achieved even with only one administration a day.

Some examples will now be described.

Example 1

A mixture of about 50 parts Povidone (as Plasdone C-15), 10 parts Lecithin Powder, Food Grade, 10 parts methylparaben and 1 part propylparaben was mixed with a range of mixtures of methyl isobutyl ketone (MIBK) and isopropylalcohol (IPA).

The results obtained are tabulated below.

| MIBK | IPA | Resulting solution |
| --- | --- | --- |
| 0 | 100 | Insoluble |
| 65 | 35 | Insoluble |
| 70 | 30 | Insoluble |
| 75 | 25 | Slight haze |
| 80 | 20 | Clear |
| 83 | 17 | Clear |
| 85 | 15 | Clear |
| 87 | 13 | Clear |
| 90 | 10 | Slight haze |
| 100 | 0 | Insoluble |

These experiments showed that the ratios of MIBK/IPA are critical. When the volume of MIBK is reduced lecithin solubility is affected by reducing the volume of IPA the solubility of Povidone is affected.

EXAMPLE 2

An experimental formulation was prepared as follows:

The following ingredients:

| | |
| --- | --- |
| Lecithin powder, Food Grade | 10 g |
| Providone USP (Plasdone C-15) | 50 g |
| Methyl paraben NF | 9 g |
| Propylparaben NF | 1 g | were added to 1 liter of 85% MIBK:15% IPA mixture, and a clear solution obtained. The solution was passed through a millipore filter to effect sterilisation. The sterile solution obtained was then aseptically combined with the following blended sterile powders:

| | |
| --- | --- |
| Amoxycillin trihydrate, sterile 80 mesh | 2.75 kg |
| Sodium citrate USP, Anhydrous, sterile | 100 g |
| Sodium chloride USP sterile | 19 g |

The solvent was then heated under vacuum until the solvent was removed leaving a free flowing granulation. This was then remilled under aseptic conditions to pass a 2 Å (0.093 inch stainless steel screen), and the product filled into sterile containers.

The stability of the product was tested and found to be comparable with commercially available AMOXI-INJECT product.

I claim:

1. In a process for the production of a sterile composition containing lecithin and polyvinyl pyrrolidone the improvement comprising admixing the lecithin and polyvinyl pyrrolidone, in a solvent comprising about 75% to 90% methyl isobutyl ketone and about 10% to 25% isopropyl alcohol, and passing the solution through a millipore filter whereby the ingredients are rendered sterile.

2. A process according to claim 1 wherein the solvent consists essentially of 80% to less than 90% methyl isobutyl ketone and 10% to less than 20% isopropyl alcohol.

3. A process according to claim 1 wherein the solvent consists essentially of about 85% methyl isobutyl ketone and 15% isopropyl alcohol.

4. A process according to claim 1 wherein a mixture of methyl p-hydroxybenzoate and propyl p-hydroxybenzoate are admixed with the lecithin and polyvinyl pyrrolidone.

5. A process according to claim 1 wherein the sterile solution produced is subsequently dispersed with an antibiotic selected from the group consisting of amoxycillin trihydrate and ampicillin trihydrate 6. A process according to claim 4 wheein the sterile solution containing lechnin, polyvinyl pyrrolidone, methyl p-hydroxybenzoate and propyl p-hydroxybenzoate is dispersed with sterile amoxycillin trihydrate.

7. A process according to claim 6 wherein the dispersion also includes a buffer and an ionic salt.

8. A process according to claim 7 wherein the buffer is sodium citrate.

9. A process according to claim 7 wherein the buffer is sodium chloride.

10. A process according to claim 1, wherein one or more preservative powders are admixed with the lecithin and polyvinyl pyrrolidone.

* * * * *